United States Patent [19]

Matsuura et al.

[11] Patent Number: 5,243,029
[45] Date of Patent: *Sep. 7, 1993

[54] ONCOFETAL STRUCTURE OF FIBRONECTIN

[75] Inventors: Hidemitsu Matsuura; Sen-Itiroh Hakomori, both of Mercer Island, Wash.

[73] Assignee: Fred Hutchinson Cancer Research Center, Seattle, Wash.

[*] Notice: The portion of the term of this patent subsequent to Jan. 16, 2007 has been disclaimed.

[21] Appl. No.: 789,422

[22] Filed: Nov. 4, 1991

Related U.S. Application Data

[63] Continuation of Ser. No. 419,720, Oct. 11, 1989, abandoned, which is a continuation of Ser. No. 849,694, Apr. 9, 1986, Pat. No. 4,894,326.

[51] Int. Cl.$^5$ .................. C07K 15/14; C07K 15/28
[52] U.S. Cl. ............................. 530/395; 530/388.25; 530/388.8; 530/388.85; 530/389.7
[58] Field of Search ................... 424/85.8; 435/70.21, 435/172.2, 240.27; 530/324–330, 380, 395, 388.25, 388.85, 388.8, 389.7

[56] References Cited

U.S. PATENT DOCUMENTS 4,894,326 1/1990 Matsuura et al. .................. 435/7

OTHER PUBLICATIONS

Ali, I. U. and T. Hunter, Structural comparison of fibronectins from normal and transformed cells, *J. Biol. Chem.* 256(14):7671–7677, 1981.

Wagner, D. D. et al., Similarities and differences between the fibronectins of normal and transformed hamster cells, *J. Biol. Chem.* 256(22):11708–11715, 1981.

Sekiguchi, K., and S-i. Hakomori, Domain structure of human plasma fibronectin: differences and similarities between human and hamster fibronectins, *J. Biol. Chem.* 258(6):3967–3973, 1983.

Hayashi, M., and K. M., Yamada, Differences in domain structures between plasma and cellular fibronectins, *J. Biol. Chem.* 256(21):11292–11300, 1981.

Atherton, B. T., and R. O. Hynes, A difference beween plasma and cellular fibronectins located with monoclonal antibodies, *Cell* 25:133–141, 1981.

Ruoslahti, E., et al., Fibronectin from human germ-cell tumors resembles amniotic fluid fibronectin, *Int. J. Cancer* 27:763–767, 1981.

Zhu, B. C-R., et al., Human placental (fetal) fibronectin: increased glycosylation and higher protease resistance than plama fibronectin, *J. Biol. Chem.*, 259(6):3962–3970, 1984.

Cossu, G., and L. Warren, Lactosaminoglycans and heparan sulfate are covalently bound to fibronectins synthesized by mouse stem teratocarcinoma cells, *J. Biol. Chem.* 258(9):5603–5607, 1983.

Murayama, K., et al., The carbohydrate structure of human fibronectins: a comparison between normal embryonic lung fibroblasts WI-38 and the SV40 virus transformed cell line VA13, *Glycoconjugate J.* 1:155–169, 1984.

Teng, M-H., and D. B. Rifkin, Fibronectin from chicken embryo fibroblasts contains covalently bound phosphate, *J. Cell Biol.* 80:784–791, 1979.

Liu, M-C., and F. Lipmann, Isolation of tyrosine-O--sulfate by pronase hydrolysis from fibronectin secreted by Fujinami sarcoma virus-infected rat fibroblasts, *Proc. Natl. Acad. Sci. USA* 82:34–37, Jan. 1985.

Sekiguchi, K., et al., Differences in domain structure between pericellular matrix and plasma fibronectins as revealed by domain-specific antibodies combined with limited proteolysis and S-cyanylation: a preliminary note, *Biochem. Biophys. Res. Comm.* 116(2):534–540, 1983.

(List continued on next page.)

Primary Examiner—David L. Lacey
Assistant Examiner—Robert D. Budens
Attorney, Agent, or Firm—Christensen, O'Connor, Johnson & Kindness

[57] ABSTRACT

Antibody defining structure present in fibronectins from tumors and fetal tissues but absent in fibronectins from normal adult tissues and plasma; useful for diagnosing and treating human cancers.

1 Claim, 13 Drawing Sheets

OTHER PUBLICATIONS

Sekiguchi, K., et al., Differences in domain structure between human fibronectins isolated from plasma and from culture supernatants of normal and transformed fibroblasts: studies with domain-specific antibodies, J. Biol. Chem. 260(8):5105–5114, 25 Apr. 1985.

Zardi, L., et al., Somatic cell hybrids producing antibodies specific to human fibronectin, Int. J. Cancer 25:325–329, 1980.

Nakabayashi, H., et al., Growth of human hepatoma cell lines with differentiated functions in chemically defined medium, Cancer Res. 42:3858–3863, 1982.

Doi, I., Establishment of a cell line and its clonal sublines from a patient with hepatoblastoma, Gann 67:1–10, 1976.

Matsuura, H., and S-i, Hakomori, The oncofetal domain of fibronectin defined by monoclonal antibody FDC-6: its presence in fibronectins from fetal and tumor tissues and its absence in those from normal adult tissues and plasma, Proc. Natl. Acad. Sci. USA 82:6517–6521, Oct. 1985.

Hakomori, S-i., and R. Kannagi, Glycosphingolipids as tumor-associated and differentiation markers, JNCI 71(2):231–251, 1983.

Kuusela, P., et al., Reactivity of hybridoma antibodies with amniotic and plasma fibronectin, Scand. J. Immunol. 12:331–337, 1980.

Matsuura, H., et al., The oncofetal structure of human fibronectin defined by monoclonal antibody FDC-6: unique structural requirement for the antigenic specificity provided by a glycosylhexapeptide, J. Biol. Chem. 263(7):3314–3322, Mar. 1988.

Atherton et al., "A Difference Between Plasma and Cellular Fibronectins located with Monoclonal Antibodies", Cell 25:133–141, Jul. 1981.

ONCOFETAL STRUCTURE OF FIBRONECTIN

This invention was made partly with Government support under Grant CA 23907 from the National Institutes of Health. The Government has certain rights in this invention.

This application is a continuation application based on prior copending application Ser. No. 07/419,720, filed on Oct. 11, 1989, now abandoned, which is a continuation of Ser. No. 06/849,694, filed Apr. 9, 1986 (U.S. Pat. No. 4,894,326).

FIELD OF THE INVENTION

This invention relates to genetic engineering methods, and more particularly to creation of monoclonal antibody defining a previously unrecognized fibronectin structure that is lost during human ontogenesis but reexpressed following oncogenic transformation, and also to use of the antibody to diagnose and treat human cancer.

BACKGROUND OF THE INVENTION

Fibronectins are a group of high molecular weight adhesive glycoproteins present in extracellular matrices and plasma. Fibronectins are produced by many types of cultured cells including fibroblasts, epithelial and endothelial cells, myoblasts, glial cells, and macrophages. Oncogenic transformation of these cells causes a marked decrease in the biosynthesis of fibronectin and its deposition in the extracellular matrix. Such cancer cells exhibit a proclivity toward dislodging from the tissue matrix and migrating in the circulatory system to form distant metastases.

Fibronectins isolated from plasma and from normal cells in culture are very similar in their chemical, biological, and immunological properties, yet there are clear differences between them in subunit size, carbohydrate structure, disulfide-dependent polymerization, solubility, ability to agglutinate sheep erythrocytes, and ability to restore normal fibroblast morphology to transformed cells. Fibronectins produced by transformed cells may also be different from those produced by normal cells. J. Biol. Chem. 256:7671–7677, 1981; J. Biol. Chem. 256:11708–11715, 1981. The basis for the molecular and functional polymorphism of fibronectins is poorly understood.

It is recognized that fibronectins are composed of multiple domains which differ in their biological activities. These domains can be separated by limited proteolysis and subsequent affinity chromatography using different ligands. For example, human plasma fibronectin can be cleaved by mild thermolysin digestion into at least four functionally distinct fragments with $M_r=155,000-145,000$ (Cell/Hep-2 domain), 44,000 (Gel domain), 24,000 (Hep-1/Fib-1 domain), and 22,000 (Fib-2 domain). J. Biol. Chem. 258:3967–3973, 1983. The domain structure of fibronectins produced by cells in culture is, however, less well-characterized than that of plasma fibronectin.

Since fibronectin is the major component of the pericellular matrix, is greatly reduced upon oncogenic transformation, and displays multi-functional properties, including opsonic activity in plasma, extensive and diversified studies have been developed toward understanding the role of this macromolecule in the structure and function of the pericellular matrix as well as in homeostatis of "milieu interieur." For example, in an extensive comparative study of the domain structure of chicken fibronectins, thermolysin fragments of plasma fibronectin and cellular fibronectin separated by various affinity columns were compared. J. Bio. Chem. 256:11292–11300, 1981. In another study, differences between plasma fibronectin and cellular fibronectin in the COOH—terminal domain were suggested by a monoclonal antibody which reacts preferentially with cellular fibronectin. Cell 25:133–141, 1981.

Also previously, Ruoslahti et al. observed a similarity in molecular weight and isoelectric point between fibronectins from human germ cell tumors and amniotic fluid and a distinctive difference from fibronectin of plasma, and suggested that such fibronectins may provide oncodevelopmental markers. Int. J. Cancer 27:763–767, 1981. A great deal of glycosylation diversity in fibronectin has been found to be dependent on fetal or transformed cell origin. J. Bio. Chem. 259:3962–3970, 1984; J. Biol. Chem. 258:5603–5607, 1983; Glycoconjugate 1:155–169, 1984. Heterogeneity of fibronectin caused by phosphorylation or sulfation may also vary with oncogenic transformation. J. Cell. Biol. 80:784–791, 1979; Proc. Natl. Acad. Sci. USA 82:34–37, 1985.

In another previous study, a highly sensitive and specific procedure for the analysis of the domain structure of fibronectins using a panel of antibodies specific for each functional domain was developed. Biochem. Biophys. Res. Comm. 116(2):534–540, 1983.

That method was very recently applied to three human fibronectins isolated from plasma and from the culture supernatants of normal and transformed fibroblasts, which were cleaved by limited proteolysis with thermolysin, trypsin, and cathepsin D as well as by S-cyanylation, followed by identification of each domain with specific antibodies. The results indicate that the COOH—terminal heparin-binding domain, Hep-2, of cellular fibronectins produced by normal and transformed fibroblasts is significantly larger than the same domain of plasma fibronectin. A significant difference in the fragments derived from the Hep-2 domain and from the gelatin-binding domain between the cellular fibronectins produced by normal and transformed fibroblasts was also demonstrated. J. Biol. Chem. 260(8):5105–5114, Issue of Apr. 25, 1985.

SUMMARY OF THE INVENTION

An IgG1 monoclonal antibody (FDC-6) was established, which defines a fibronectin structure or structures located between the "Hep-2" and the "Fib-2" domains in the COOH—terminal region of fibronectins isolated from hepatoma, sarcoma, and fetal fibroblasts. A systematic study with this antibody indicates the presence of two classes of human fibronectin. (i) Fibronectin from fetal connective tissue, placenta, amniotic fluid, hepatoma, and colon carcinoma as well as cell lines from fetal tissues (WI-38), hepatomas (HuH-6 and HuH-7), and sarcoma (VA13) was characterized by the presence of the FDC-6 defined structure and by a high molecular weight (subunit $M_r$, 310,000–335,000). (ii) In contrast, fibronectin from normal adult tissues and plasma was characterized by a lower molecular weight (subunit $M_r$, 285,000–295,000) and lack of reactivity with FDC-6, and is therefore devoid of the FDC-6 defined structure. The FDC-6 defined structure is hereby called the "oncofetal structure," and fibronectin containing this structure is hereby called "oncofetal fibronectin." Fibronectin from normal adult tissues and plasma, lacking the oncofetal structure, is hereby called "normal fibronectin." Development of fibronectin from fetal to adult form is associated with loss of the oncofetal structure defined by the FDC-6 antibody, and oncogenic transformation is associated with activation in synthesis of the oncofetal structure defined by the FDC-6 antibody. Since the structure defined by FDC-6 antibody expressed in oncofetal fibronectin is a useful marker of cancer, it is contemplated that the FDC-6 antibody and other antibodies raised against the oncofetal fibronectin structure will be useful for diagnosing human cancer and for monitoring and implementing various cancer treatments.

DESCRIPTION OF THE PREFERRED EMBODIMENT

The murine monoclonal antibody FDC-6 was established, as described below, following immunization with fibronectin isolated from human hepatoma cells. The hybridoma ATCC No. HB 9018 was selected by positive reactivity of its antibody (FDC-6) with fibronectins from hepatoma, fibrosarcoma, and fetal fibroblasts (WI-38) and by negative reactivity with fibronectin from plasma. The antibody FDC-6 defines a specific structure that is present in fibronectins from tumors and fetal tissues but is absent in fibronectins from normal adult tissues and plasma.

Figure 1:
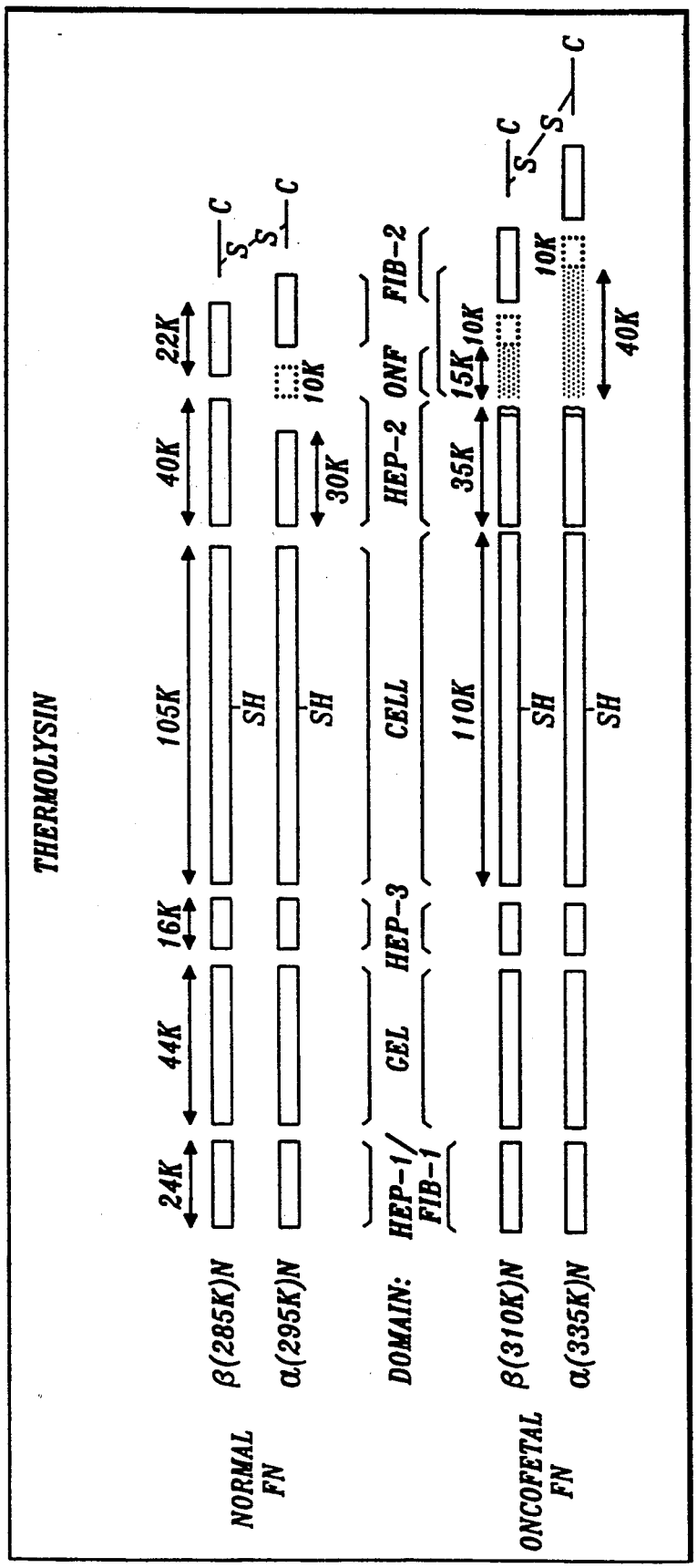
FIGS. 1-3 present schematic drawings of human fibronectin domains released by limited proteolysis with thermolysin (FIG. 1), trypsin (FIG. 2), and cathepsin D (FIG. 3), wherein the location of the oncofetal structure is indicated by shaded bar.
Figure 2:
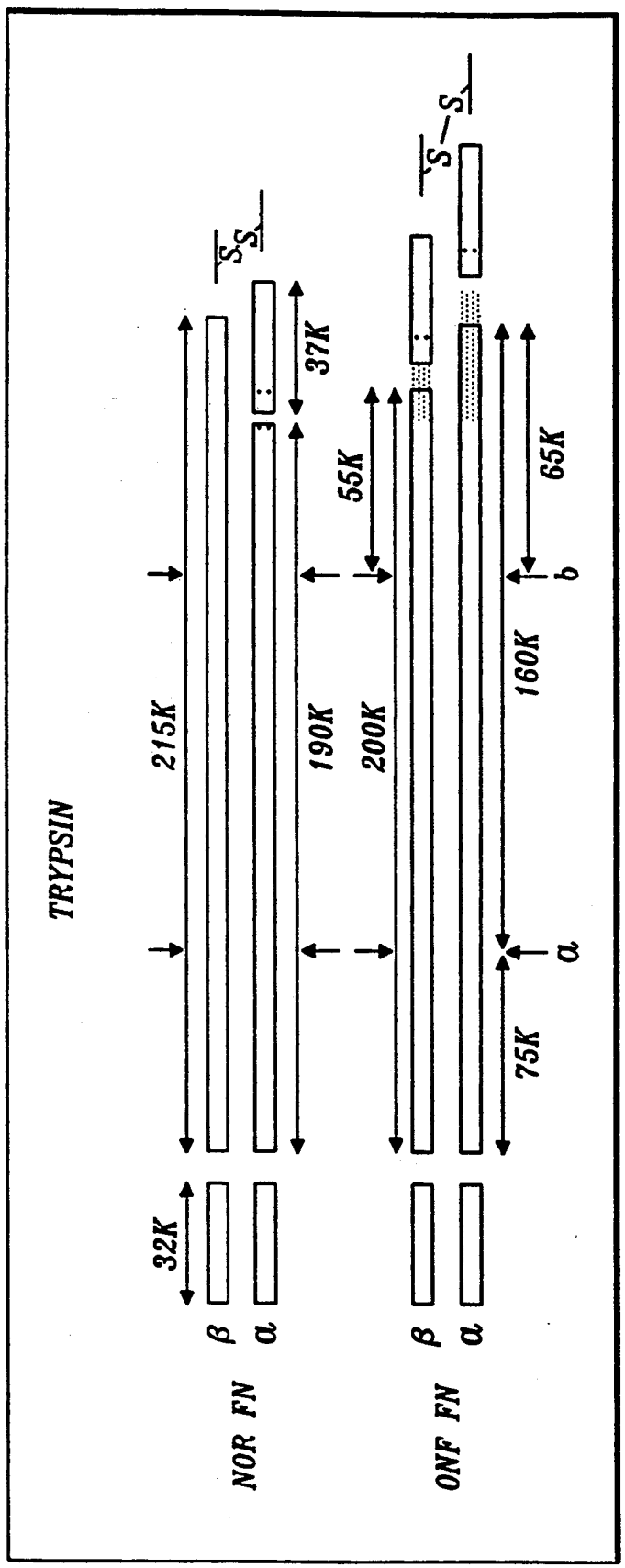
Figure 3:
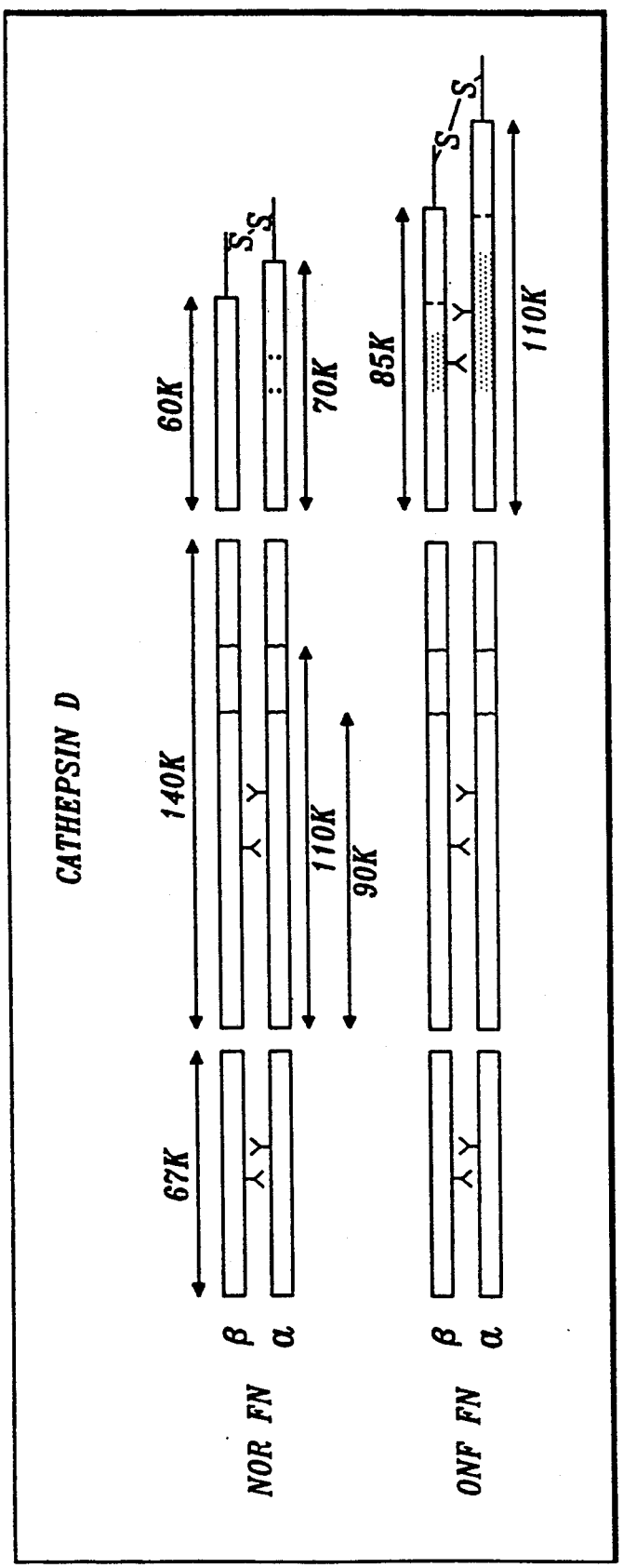

FIGS. 1-3 present schematic drawings of human fibronectin domains released by limited proteolysis with thermolysin, trypsin, and cathepsin D. The location of the oncofetal structure is indicated by shaded bar. Molecular weights are shown as $M_r \times 10^{-3}$. Referring to FIG. 1, thermolysin releases six domains from normal fibronectin: $M_r$ 24,000 (Hep-1/Fib-1), $M_r$ 44,000 (Gel), $M_r$ 16,000 (Hep-3), $M_r$ 105,000 (Cell), $M_r$ 30,000–40,000 (Hep-2), and $M_r$ 22,000 (Fib-2). The size of Hep-2 is $M_r$ 30,000 from $\alpha$ and $M_r$ 40,000 from $\beta$, and the $\delta$-chain may contain an undetectable $M_r$ 10,000 domain based on calculation. Similar fragments are released by thermolysin from oncofetal fibronectin, except for the size of the Hep-2 domain ($M_r$ 35,000, heterogenous). The FDC-6 antibody does not react with any of the domains released by thermolysin from normal or oncofetal fibronectins.

Referring to FIG. 2, trypsin digestion releases $M_r$ 37,000 (containing Fib-2 domain), $M_r$ 32,000 (Hep-1/Fib-1), and large $M_r$ 215,000–190,000 fragments from normal fibronectin, and an $M_r$ 200,000 fragment from oncofetal fibronectin. Only the $M_r$ 200,000 fragment from oncofetal fibronectin and no fragments from normal fibronectin are stained by FDC-6. In addition, a strong staining was associated with smaller fragments ($M_r$ 120,000–160,000 and $M_r$ 55,000–65,000) derived from the middle domain by cleavage at points "a" and "b." Those fragments contained the oncofetal structure.

Referring to FIG. 3, only the $M_r$ 85,000 and $M_r$ 110,000 fragments released by cathepsin D, which represent the COOH-terminal region of oncofetal fibronectin, are stained with FDC-6. The corresponding $M_r$ 60,000 and $M_r$ 70,000 fragments from normal fibronectin were not so stained.

The location of the oncofetal structure (indicated by shaded bar in FIGS. 1-3) is based on: (i) the presence of FDC-6 reactivity at the COOH-terminal region released by cathepsin D, i.e., positive in $M_r$ 85,000–110,000 fragments from oncofetal fibronectin and negative in $M_r$ 60,000–70,000 fragments from normal fibronectin; and, (ii) the absence of FDC-6 reactivity in the Hep-2 and Fib-2 domains released by thermolysin. The size of the oncofetal structure is tentative and is based on calculation.

In a systematic study, fibronectins from fetal connective tissue, placenta, amniotic fluid, hepatoma, and colon carcinoma as well as cell lines from fetal tissues (WI-38), hepatomas (HuH-6 and HuH-7), and sarcoma (VA13) were characterized by the presence of the FDC-6-defined oncofetal structure. In contrast, fibronectins from normal adult tissues, including skin, paravertebral connective tissue, and large intestine, and plasma were devoid of the FDC-6-defined oncofetal structure.

These results suggest that switching from oncofetal fibronectin synthesis to normal fibronectin synthesis is associated with human ontogenesis, and that the reverse process is associated with oncogenesis.

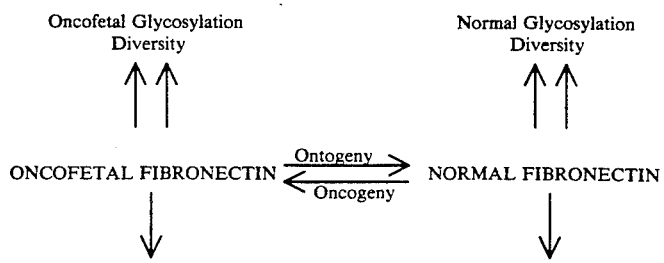

Phosphorylation
Sulfation
Diversity

-continued

Phosphorylation
Sulfation
Diversity

Since the structure defined by FDC-6 antibody expressed in oncofetal fibronectin is a useful marker of cancer, the FDC-6 antibody and other immunological binding partners (antibodies, antigen-binding fragments, chimaeras, etc.) directed against the oncofetal fibronectin structure are of practical value in diagnostic tests and in monitoring and implementing various cancer treatments. The FDC-6 antibody can be coupled to a radionuclide and introduced into the body of a mammal to image cancer cell location and/or implement radiotherapy. For example, a radionuclide such as I-123 can be coupled to the antibody FDC-6 using standard methodologies, such as those employing the Bolton-Hunter reagent. The radiolabeled antibody can be admixed in a suitable carrier solution and introduced, e.g., intravenously, into the body of a mammal. The body can thereafter be scanned with a scintillation detector such as a gamma camera to localize tumor tissues such as metastases bearing oncofetal fibronectin reactive with the radiolabeled antibody. The antibody FDC-6 is also suitable for implementing cancer immunological therapy. The antibody can be coupled to a radionuclide or anti-tumor drug, such as mitomycin, and introduced into the body of an adult mammal in order to differentially deliver the radionuclide or drug to tumor tissues bearing oncofetal fibronectin.

The FDC-6 or other specific antibody can also be coupled to a detectable marker for immunohistological detection of tumor cells that express oncofetal fibronectin. The detectable marker can be selected from among fluorophores, enzymes, chromophores, coenzymes, chemiluminescent materials, enzyme inhibitors, paramagnetic metals such as gadolinium, and radionuclides that are known in the art. Biopsied cells can be contacted with the antibody-marker conjugate, and any detectable marker that becomes sequestered on the cells can be detected by standard techniques after unreacted antibody is removed. It is contemplated that, with the development of highly sensitive immunoassays, oncofetal fibronectin can also be detected as a tumor-associated marker in blood serum using the FDC-6 or other specific antibody.

The FDC-6 antibody, as well as other antibodies raised against the oncofetal structure, can be packaged in kits useful for assaying the presence of oncofetal fibronectin, or for delivering therapeutic agents to the immediate vicinity of cells that express oncofetal fibronectin.

The representative HB 9018 hybridoma that produces the antibody designated FDC-6 was deposited on Feb. 12, 1986, at the American Type Culture Collection, 12301 Parklawn Drive, Rockville, Md. 20852.

The following Examples are presented to illustrate the advantages of the present invention and to assist one of ordinary skill in making and using the same. These Examples are not intended in any way to otherwise limit the scope of the disclosure or the protection granted by Letters Patent hereon.

EXAMPLE 1

Preparation of fibronectins.

Fibronectins from plasma and from the culture medium of fibroblasts, hepatoma, and fibrosarcoma cells were prepared by gelatine-Sepharose column chromatography as described in Int. J. Cancer 20: 1-5, 1977, hereby incorporated by reference.

Tissue fibronectin fractions were prepared by their insolubility in neutral detergent under nonreducing conditions as follows. Tissues were minced with scissors and homogenized in a Dounce homogenizer in a sample buffer made up of phosphate-buffered saline (8.1 mM $Na_2HPO_4$, 1.5 mM $KH_2PO_4$, 137 mM NaCl, 2.7 mM KCl, pH 7.2) containing 0.5% Nonidet P-40 detergent, 0.1% $NaDodSO_4$, 1 mM phenylmethylsulfonyl fluoride, and 0.5 mM EDTA. The homgenate was centrifuged, and the precipitate was washed twice in the phosphate-buffered saline. Washing was followed by centrifugation at 10,000×g for 30 min. The precipitate thus obtained was suspended and dissolved by heating in a boiling water bath for 5 min. in sample buffer containing 5% 2-mercaptoethanol and 2% $NaDodSO_4$ (Nature 227: 680-685, 1970).

EXAMPLE 2

Immunoblotting of fibronectins.

Tissue extract containing fibronectin prepared as in Example 1 was analyzed on gel electrophoresis in 0.2% $NaDodSO_4$ employing 9.5% and 6.5% polyacrylamide under reducing conditions, followed by transfer onto nitrocellulose sheets and blotting with monoclonal antibodies. J. Biol. Chem. 260:5105-5114, 1985; Cancer Res. 42:3858-3863, 1985; Proc. Natl. Acad. Sci. USA 76:4350-4354, 1979.

Antibodies IST-1 and IST-4 (Int. J. Cancer 25: 325-329, 1980) were donated by Luciano Zardi and Annalisa Siri (Istituto Nazionale per la Ricerca sul Cancro, Genova, Italy). IST-1 defines the "Hep-2" domain (Biochem. Biophys. Res. Commun. 116: 534-540, 1983; J. Biol. Chem. 260: 5105-5114, 1985) and IST-4 defines a part of the "Cell" domain.

Monoclonal antibody FDC-6 was prepared as described below.

Another IgG1 antibody (FDZ), which has a similar reactivity to that of IST-4 and defines a part of the Cell domain, was also established as described in Example 3.

EXAMPLE 3

Preparation of monoclonal antibody FDC-6.

Monoclonal antibody FDC-6 was established after immunization of BALB/c mice with fibronectin isolated from HuH-6 human hepatoma cells. HuH-6 and HuH-7 human hepatoma cells (Cancer Res. 42: 3858-3863, 1985) were donated by Jiro Sato (Okayama University, Okayama, Japan). Fibronectin was isolated from the HuH-6 hepatoma cells as described in Example 1. The isolated fibronectin, coated on acid-treated *Salmonella minnesota*, was used as immunogen according to the method described in J. Biol. Chem. 257: 12752-12756, 1982, hereby incorporated by reference. Specifically, about 5 μg of the fibronectin fraction was admixed with 2 mg *S. minnesota* and injected intravenously into BALB/c mice on Day 0, and 2 μg of the fibronectin fraction mixed with 2 mg of *S. minnesota* was injected every four days thereafter, totaling seven intravenous injections. On the fourth day after the last injection, spleen cells were harvested and fused with SP-1 mouse myeloma cells. Hybridomas were cloned on 96-well plates (Dynatech Immunolon plate, Dynatech Laboratories, Alexandria, Va.) coated with the same fibronectin fraction (10 μg/well), cholesterol (30 μg/well), and lecithin (50 μg/well). Cloning was performed repeatedly.

The hybridoma secreting the antibody designated FDC-6 was selected, and the specificity of the antibody FDC-6 was characterized, as described in Examples 4, 5, and 6.

EXAMPLE 4

Binding specificity of monoclonal antibody FDC-6.

The hybridoma secreting the FDC-6 antibody was selected by positive reactivity of its antibody with fibronectins from (i) human hepatomas HuH-6 and HuH-7 and (ii) normal human fetal lung WI-38 fibroblasts, and by negative reactivity with plasma fibronectin. This binding specificity of the monoclonal antibody FDC-6 was determined by solid-phase radioimmunoassay systems with antigen dilution, antibody dilution, and competitive inhibition of antibody binding on solid-phase fibronectin. Solid-phase radioimmunoassay was performed on vinyl strips (Costar Laboratories, Cambridge, Mass.) according to the procedure described in FEBS Lett. 142: 243-246, 1982.

Figure 4:
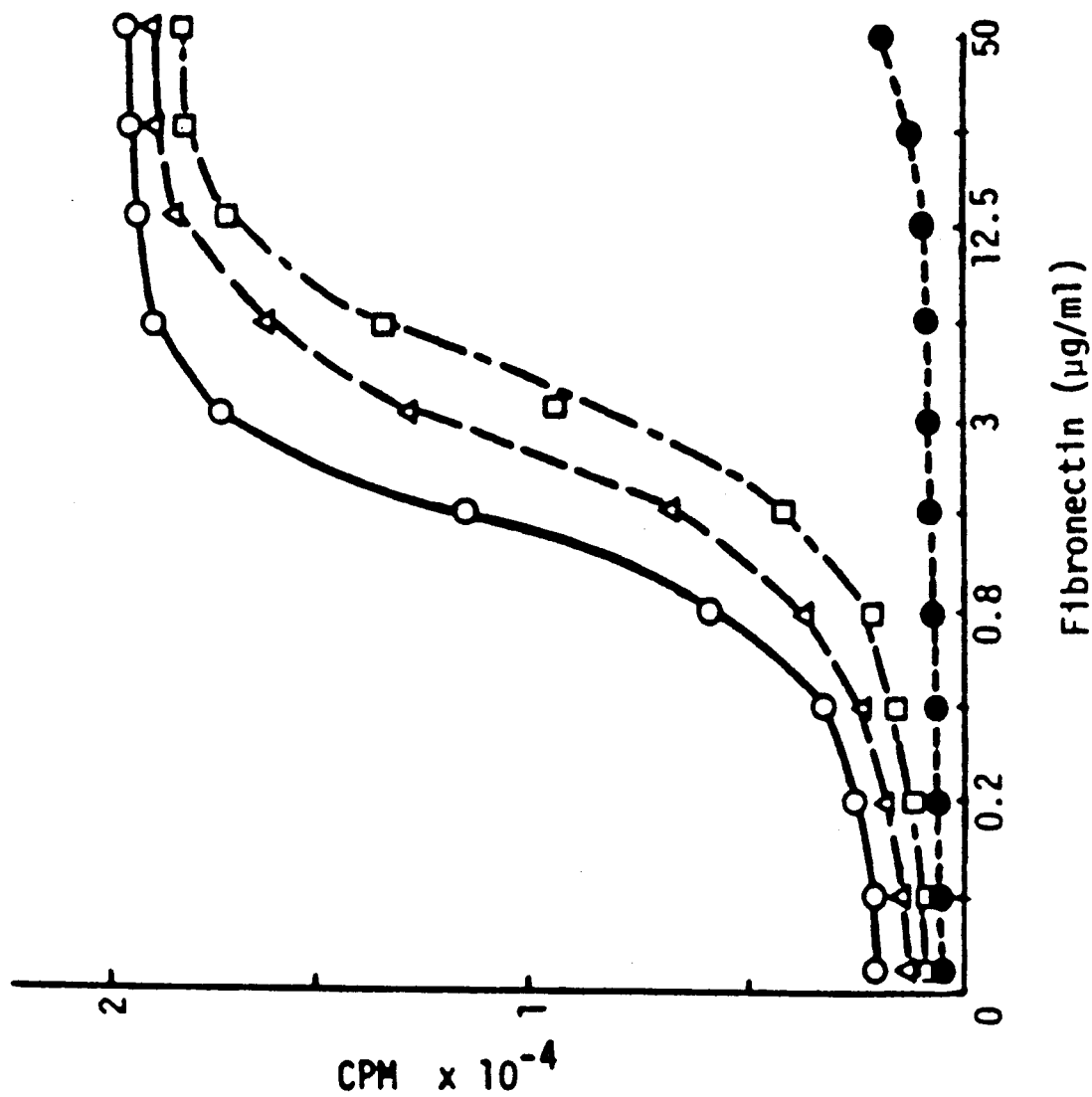
FIGS. 4-6 present three panels of data showing the binding specificity of monoclonal antibody FDC-6 with various fibronectins as determined by solid phase radioimmunoassays with antigen dilution (FIG. 4), antibody dilution (FIG. 5), and competitive inhibition of antibody binding (FIG. 6), all as described in Example 4.

FIG. 4 presents representative results of the antibody dilution assay. Binding activities of the FDC-6 antibody, expressed on the ordinate as relative counts per minute, are shown for different concentrations (FN, μg/ml) of various fibronectins adsorbed on a plastic surface. The various fibronectins were prepared as described in Example 1 and are here identified by the following symbols: solid circles, plasma fibronectin; open circles, fibronectin isolated from culture medium of hepatoma HuH-7; open triangles, fibronectin from culture medium of hepatoma HuH-6; open squares, fibronectin from culture medium of WI-38 fibroblasts.

Figure 5:
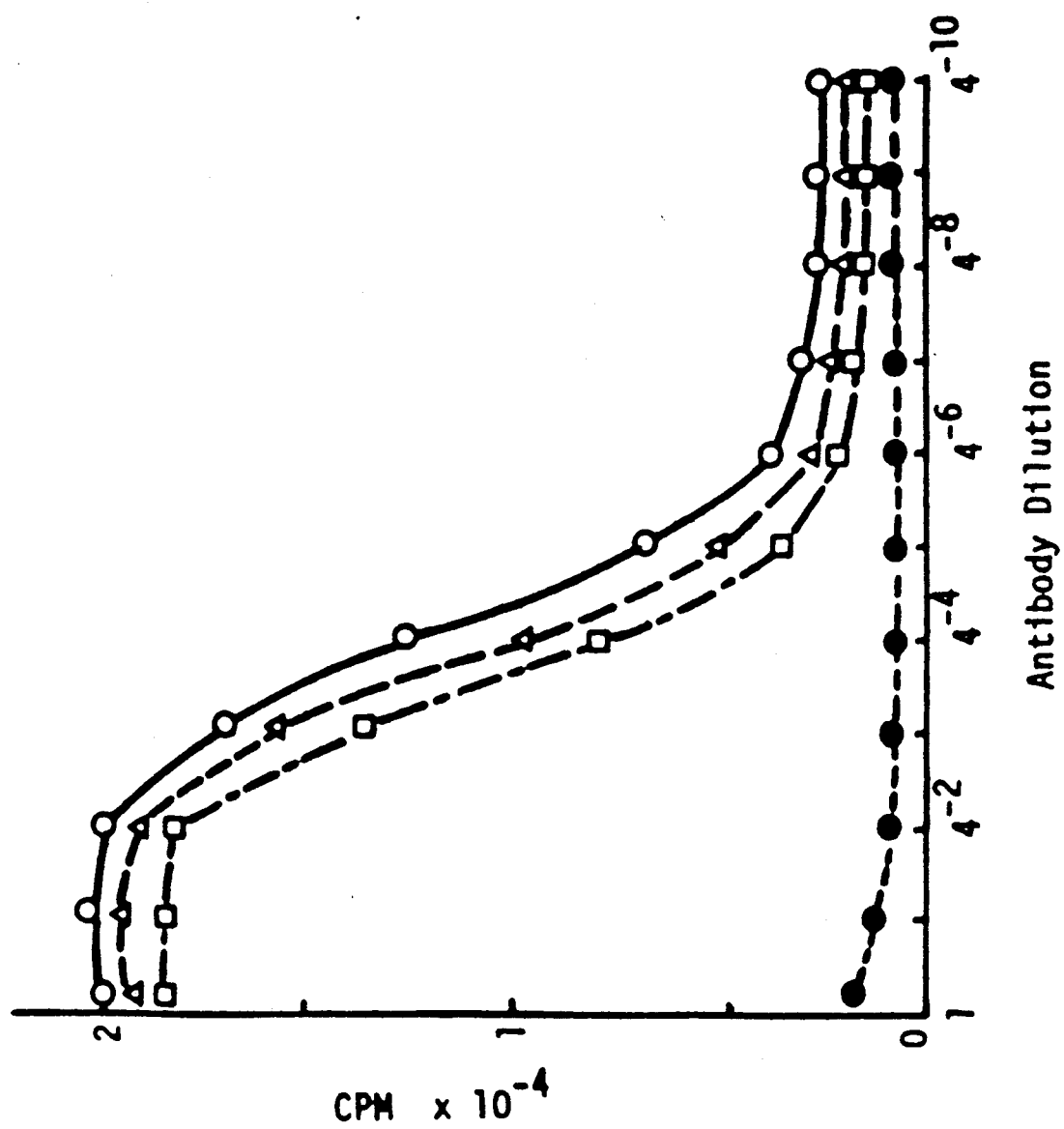

FIG. 5 presents similar results from a representative antigen dilution assay. Antibody binding activity to the various fibronectins coated with constant concentration (50 μg/ml) is shown for various concentrations of FDC-6 antibody. The various fibronectins are identified by the same symbols as above.

Figure 6:
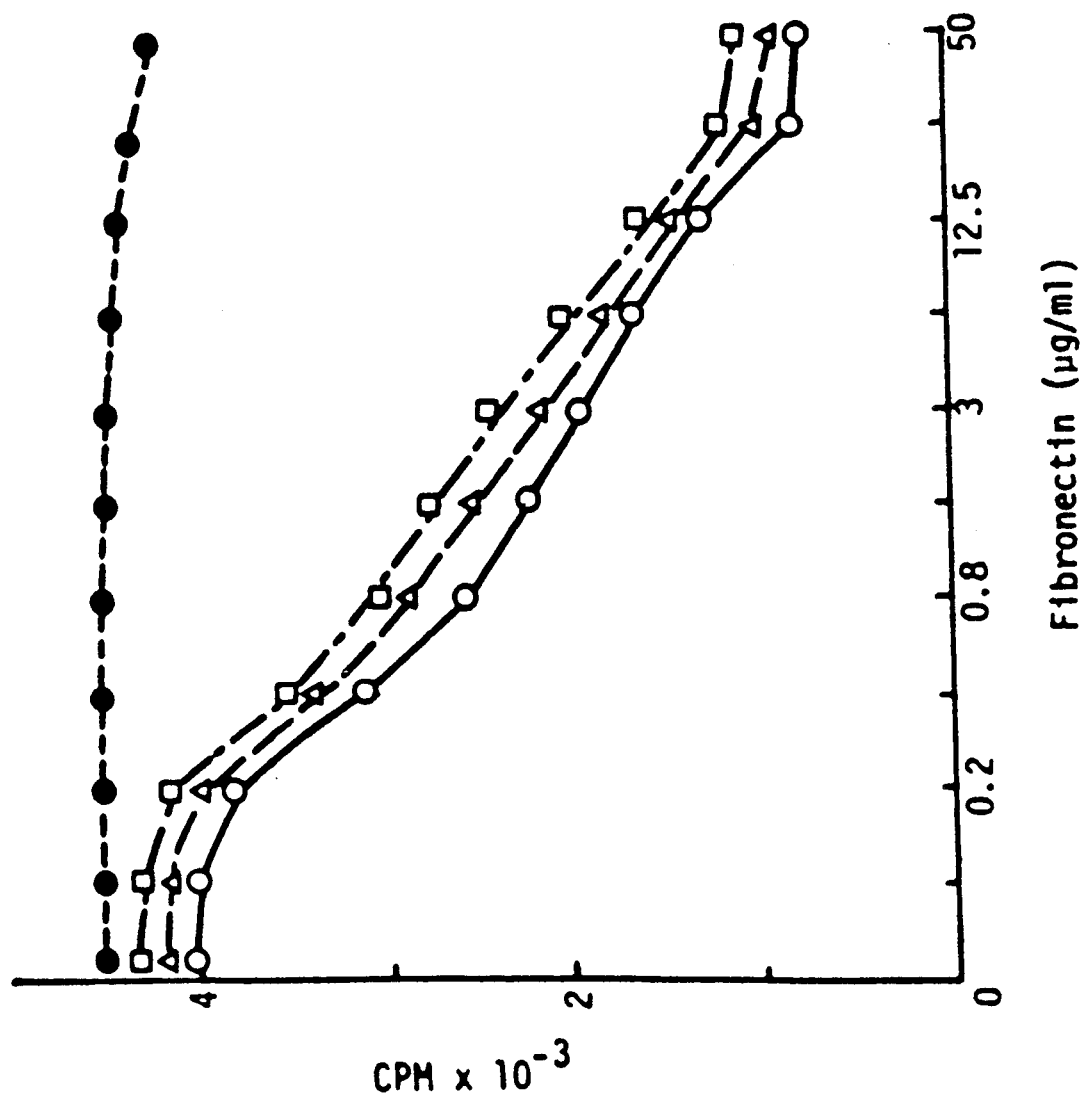

FIG. 6 shows competitive inhibition of FDC-6 antibody binding to hepatoma fibronectin (HuH-7) coated on a plastic surface with a concentration of 50 μg/ml. The culture supernatant of FDC-6 cells diluted 1000 times was used as antibody. Aliquots (50 μl) of diluted antibody were mixed with increasing concentrations (FN, μg/ml) of various fibronectins followed by transfer of the mixture onto a well coated with fibronectin from HuH-7 hepatoma. Symbols are the same as above.

EXAMPLE 5

Domain recognition of monoclonal antibody FDC-6.

The location of the reactive site of the FDC-6 antibody was determined by limited proteolysis of fibronectins from plasma, WI-38 fibroblasts, and HuH-6 and HuH-7 hepatomas by thermolysin, trypsin, and cathepsin D, followed by electrophoretic transfer blotting with various antibodies directed to Fib-1/Hep-1, Gel, Hep-3/Cell, Hep-2, and Fib-2 domains.

Fragmentation of the various fibronectins by thermolysin, trypsin, and cathepsin D digestions were performed as described in J. Biol. Chem. 260(8): 5105-5114, 1985, see the appended experimental procedures. SDS-polyacrylamide gel electrophoresis of the cleaved fragments, followed by electrotransfer and immunostaining were also performed as described.

Figure 7:
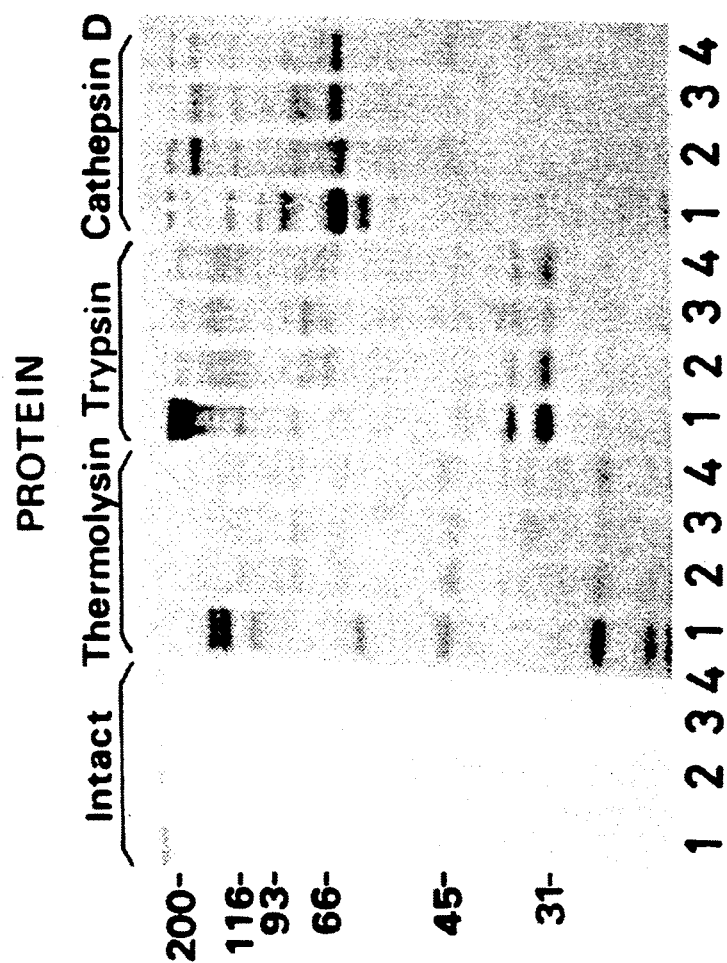
FIGS. 7-8 present representative immunoblotting patterns of various fibronectin fragments (FIG. 7) with monoclonal antibody FDC-6 (FIG. 8), as described in Example 5.
Figure 8:
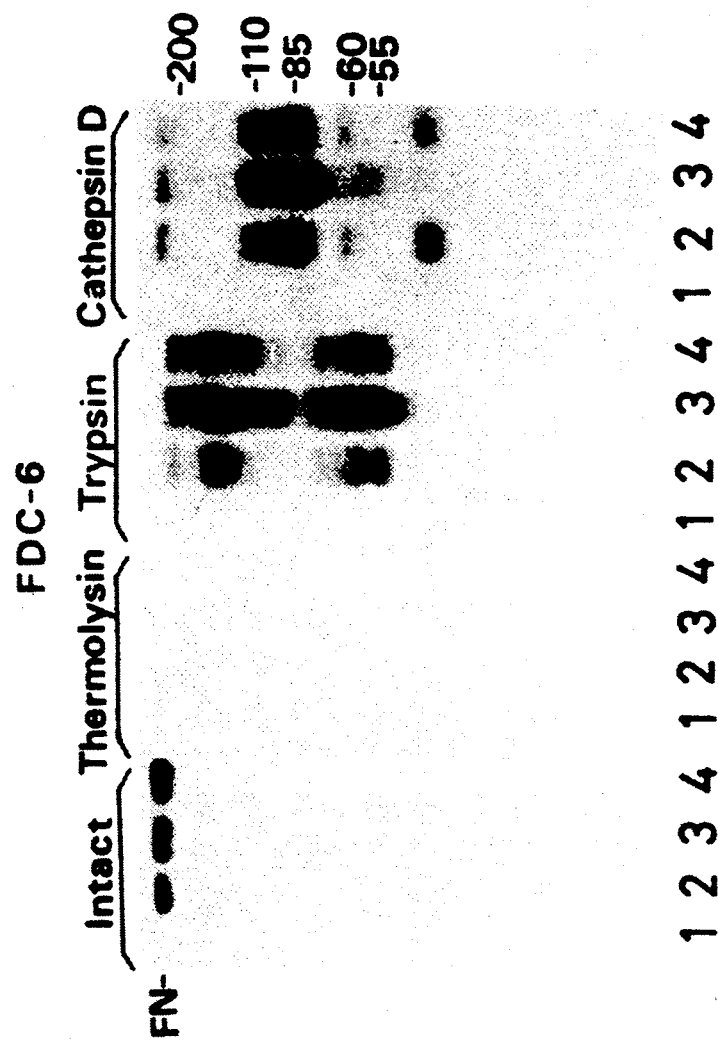

FIGS. 7-8 show representative immunoblotting patterns of proteolytic fragments of various fibronectins with monoclonal antibody FDC-6. FIG. 7 shows protein staining with fast green. FIG. 8 shows an immunoblotting pattern of the same gel as in FIG. 7 with monoclonal antibody FDC-6. The fragmentation patterns induced by each enzyme are identified at the top of the panels. The various fibronectins are identified by lane numbers in FIGS. 7-8 as follows: lanes 1, plasma fibronectin; lanes 2, fibronectin from culture medium of WI-38 fibroblasts; lanes 3 and lanes 4, fibronectins from culture media of hepatomas HuH-6 and HuH-7, respectively. Molecular weights are shown as $M_r \times 10^{-3}$.

The fragments defined by FDC-6 released by trypsin and cathepsin D were similar to but obviously different from those defined by the IST-1 antibody (J. Biol. Chem. 260: 5105-5114, 1985), since none of the fragments released by thermolysin was reactive with the FDC-6 antibody (FIG. 8, Thermolysin). The Hep-2 domain ($M_r$ 30,000-40,000 reactive with antibody IST-1), the Fib-2 domain ($M_r$ 22,000) released by thermolysin, and the Fib-2 domain ($M_r$ 37,000) released by trypsin treatment were not reactive with FDC-6, whereas the COOH-terminal region released by cathepsin D ($M_r$ 85,000 and $M_r$ 110,000), which showed disulfide-dependent linkage (J. Biol. Chem. 260:5109-5114, 1985), was reactive with FDC-6 (FIG. 8, Cathepsin D). A large $M_r$ 200,000 fragment, and $M_r$ 120,000-160,000 and $M_r$ 55,000-65,000 degradation products released by trypsin treatment were reactive with FDC-6 (FIG. 8, Trypsin). These FDC-6-positive trypsin fragments represent the COOH-terminal side of the middle domain after cleavage of the $M_r$ 37,000 fragment (possible cleavage points are indicated by arrows in FIG. 2). Thus, the structure reactive with the FDC-6 antibody must be located between the Hep-2 and Fib-2 domains within the COOH-terminal region of fibronectins isolated from the culture medium of hepatoma and WI-38 fibroblasts. This oncofetal structure with FDC-6 reactivity is highly susceptible to digestion with thermolysin and is not detectable after thermolysin digestion.

EXAMPLE 6

Further characterization of the fibronectin domain recognized by antibody FDC-6.

To determine whether the FDC-6 antibody reacts with a carbohydrate determinant, fibronectin coated on a plastic surface was treated with sodium periodate/borohydride (J. Immunol. Methods 78:143-153, 1985) followed by reaction with the FDC-6 antibody as described above. The FDC-6 reactivity was observed to be resistant to treatment with sodium periodate/borohydride and may therefore represent a polypeptide region. In addition, the oncofetal structure recognized by FDC-6 did not react with various anticarbohydrate antibodies that define oncofetal carbohydrate determinants (data not shown).

EXAMPLE 7

Determination of immunoglobulin subclass.

The immunoglobulin subclass of the antibody FDC-6 was determined with subclass-specific antibodies purchased from Cappel Laboratories, Cochranville, Pa. FDC-6 is an IgG1 antibody.

EXAMPLE 8

Immunoblotting pattern of various fibronectins with antibody FDC-6.

Figure 10:
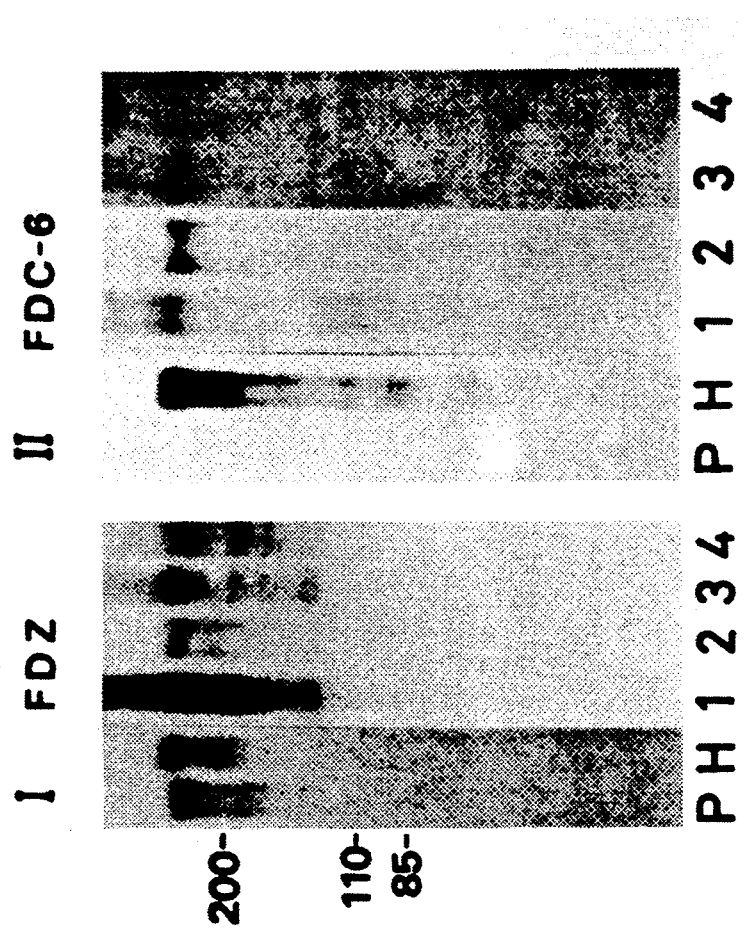
Figure 11:
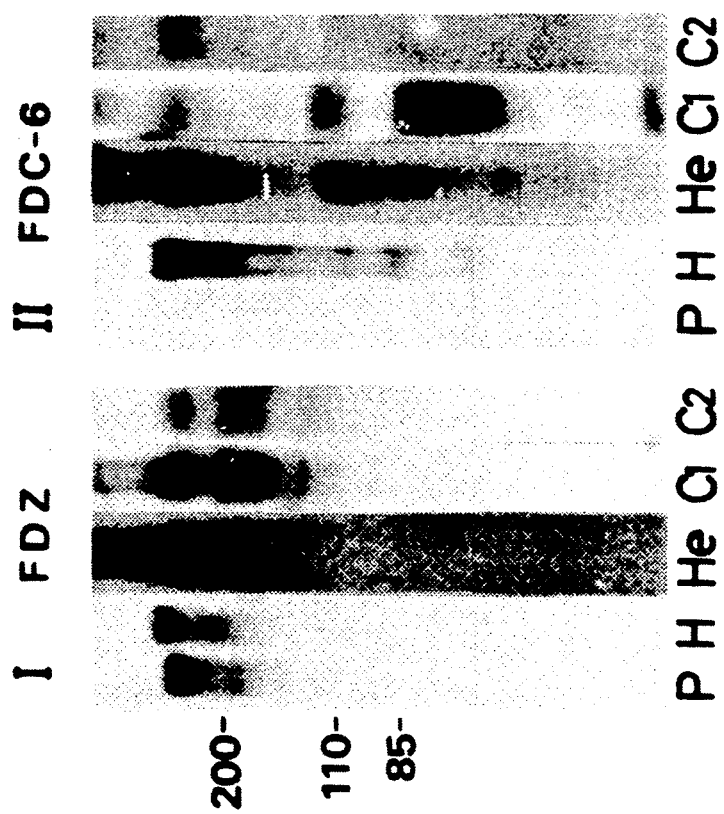
Figure 12:
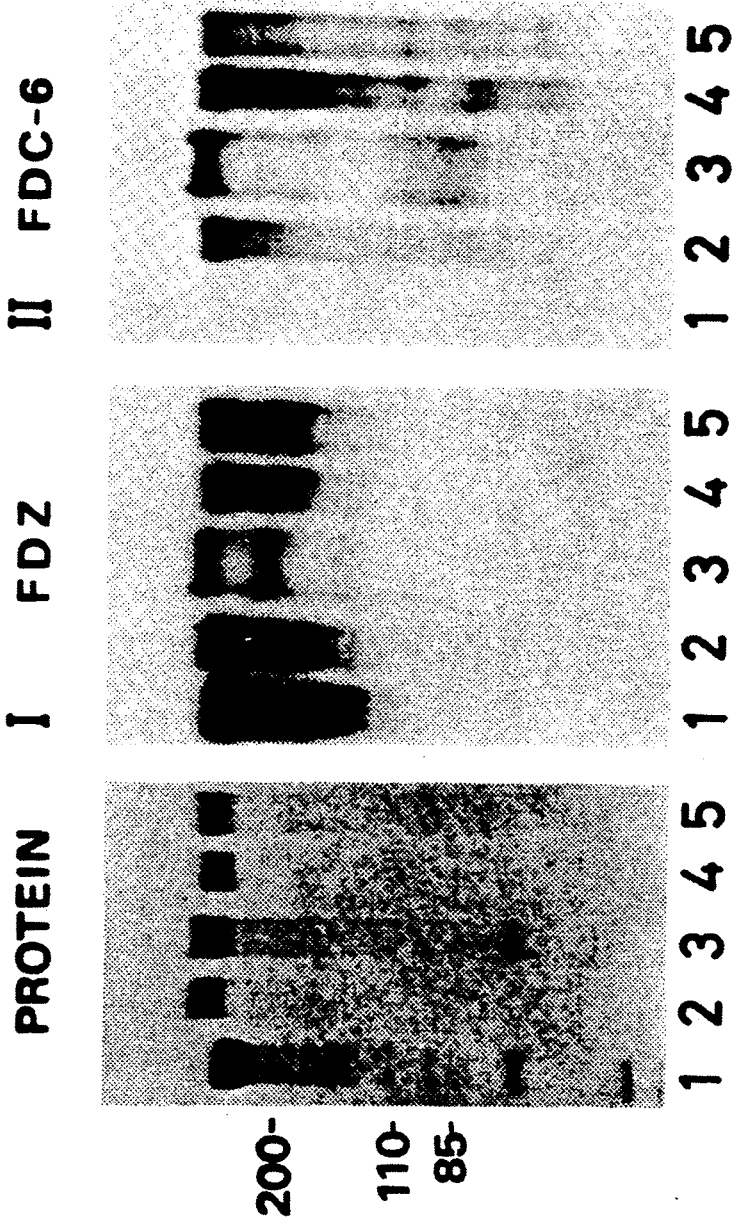

FIGS. 9-12 show immunblotting patterns of various fibronectins extracted from human adult tissues (FIG. 9), human fetal tissues (FIG. 10), hepatomas and colon adenocarcinomas (FIG. 11), and various cell lines from fetal tissue and hepatomas (FIG. 12). In each panel, group I was blotted with monoclonal antibody FDZ and replicate group II was blotted with monoclonal antibody FDC-6. Molecular weights are shown as $M_r \times 10^{-3}$. The various fibronectins are identified below for each panel.

Figure 9:
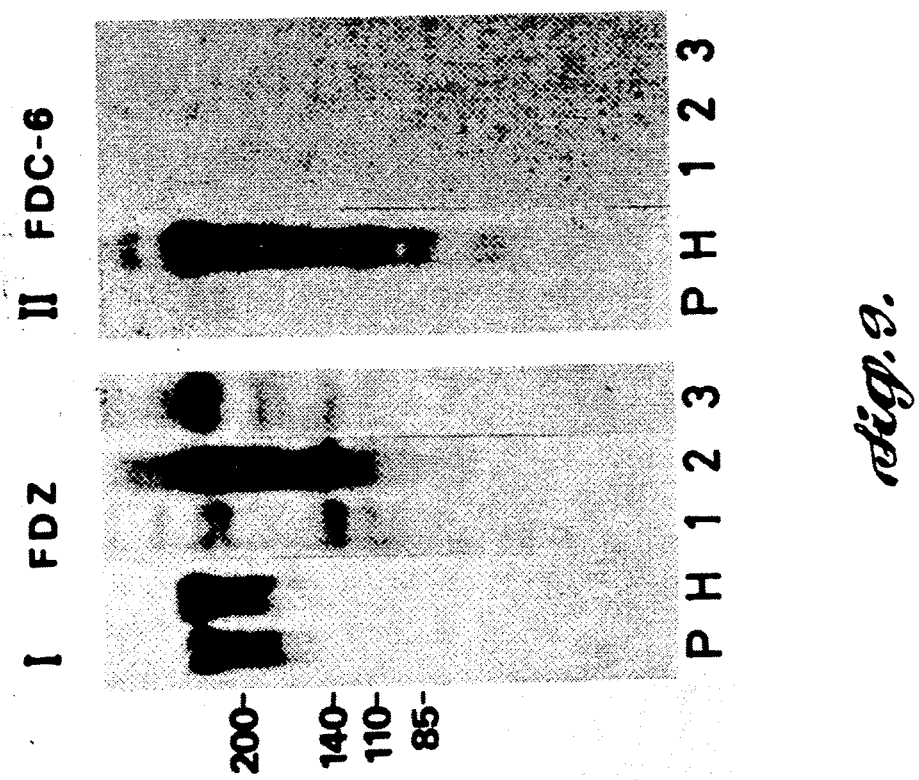
FIGS. 9-12 present representative immunoblotting patterns of fibronectins extracted from human and adult tissues with both the Cell-domain recognizing antibody FDZ and with the oncofetal-structure recognizing antibody FDC-6, as described in Example 8; and, FIG. 13 is a graphical display of data showing the quantitative reactivity of various fibronectins with monoclonal antibody FDC-6, as described in Example 9.

FIG. 9 shows absence of fibronectin reaction with the FDC-6 antibody in various adult tissues. Fibronectins are identified in FIG. 9 as follows: lanes P, plasma fibronectin; lane H, hepatoma fibronectin from culture medium of HuH-7 cells. These two samples were used as reference controls; note that lane P was not stained by FDC-6. Lane 1, skin fibronectin; lane 2, paravertebral connective tissue fibronectin; lane 3, large intestine fibronectin.

Fibronectins from adult human plasma, connective tissue (paravertebral region), and skin showed an obvious reactivity with the FDZ antibody, which defines a region in the Cell domain, and these fibronectins had the same molecular weight as those of plasma. In contrast, none of these fibronectins from adult tissues and plasma reacted with monoclonal antibody FDC-6. Extracts of normal adult spleen, kidney, and liver also gave fibronectin bands with similar reactivities as above, i.e., negative with FDC-6 and positive with the FDZ antibody (data not shown).

FIGS. 10-12 show reactivity of the FDC-6 antibody with fibronectins from placenta amniotic fluid, various fetal tissues, tumor tissues, and culture cells. The fibronectins are identified as follows.

FIG. 10: lanes P and H, the same reference controls as in FIG. 9; lanes 1, fibronectin from placenta; lanes 2, fibronectin from amniotic fluid; lanes 3, fibronectin from fetal connective tissue (carcass tissue mass from a 70-day embryo); lanes 4, fibronectin from subcutaneous connective tissue of a 100-day fetus.

FIG. 11: lanes P and H, the same as in FIGS. 9 and 10; lanes He, fibronectin from hepatoma tissue; lanes C1, fibronectin from colon cancer case 1; lanes C2, fibronectin from colon cancer case 2. The two colon cancers were both adenocarcinomas. The low molecular weight components in lanes He and C1 of group II were degradation products of an endogenous cathepsin-like protease, which was not inhibited by protease inhibitor added to the extracts.

FIG. 12: lanes 1, plasma fibronectin; lanes 2, fibronectin from the culture medium of WI-38 fibroblasts; lanes 3, fibronectin from the culture medium of VA13 sarcoma cells; lanes 4, fibronectin from the culture medium of HuH-6 hepatoma cells; lanes 5, fibronectin from the culture medium of HuH-7 hepatoma cells.

Fibronectins from placenta, amniotic fluid, fetal connective tissue, and fetal skin were reactive with the FDZ and FDC-6 antibodies (FIG. 10). Extracts of some hepatomas and colon carcinoma tissues (FIG. 11) as well as cell lines derived from fetal lung tissue (WI-38), hepatomas (HuH-6 and HuH-7), and sarcoma (VA13) (FIG. 12) contained fibronectin reactive with the FDZ and FDC-6 antibodies. However, some hepatoma and carcinomas did not contain FDC-6 reactive fibronectin but contained FDC-6-negative, FDZ-positive fibronectin (data not shown).

EXAMPLE 9

Quantitative reactivity of fibronectins from adult, fetal, and cancer tissues.

To quantitatively determine the reactivity of fibronectins from various sources with the FDC-6 antibody, the binding reactivity of the FDC-6 antibody per $\mu g$ of fibronectin was calculated as follows. Since the binding activity of the FDZ antibody with fibronectins from various sources was observed to correlate well with the chemical quantity blotted onto nitrocellulose sheets, the chemical quantity of each fibronectin was determined on gel electrophoresis followed by electrophoretic transfer blotting (Proc. Natl. Acad. Sci. USA 76:4350-4354, 1979). Multiple samples separated on gels and blotted onto nitrocellulose sheets reacted with the FDC-6 antibody as well as the FDZ antibody. Simultaneously, 1-5 $\mu g$ of purified fibronectin from plasma and HuH-7 hepatoma were blotted onto nitrocellulose sheets after naDodSO$_4$ gel electrophoresis. The binding activity of FDZ and FDC-6 was thereby correlated with the chemical quantity of fibronectin. The binding activity with omission of fibronectin and that with omission of the primary antibody were used as the background to be subtracted.

Figure 13:
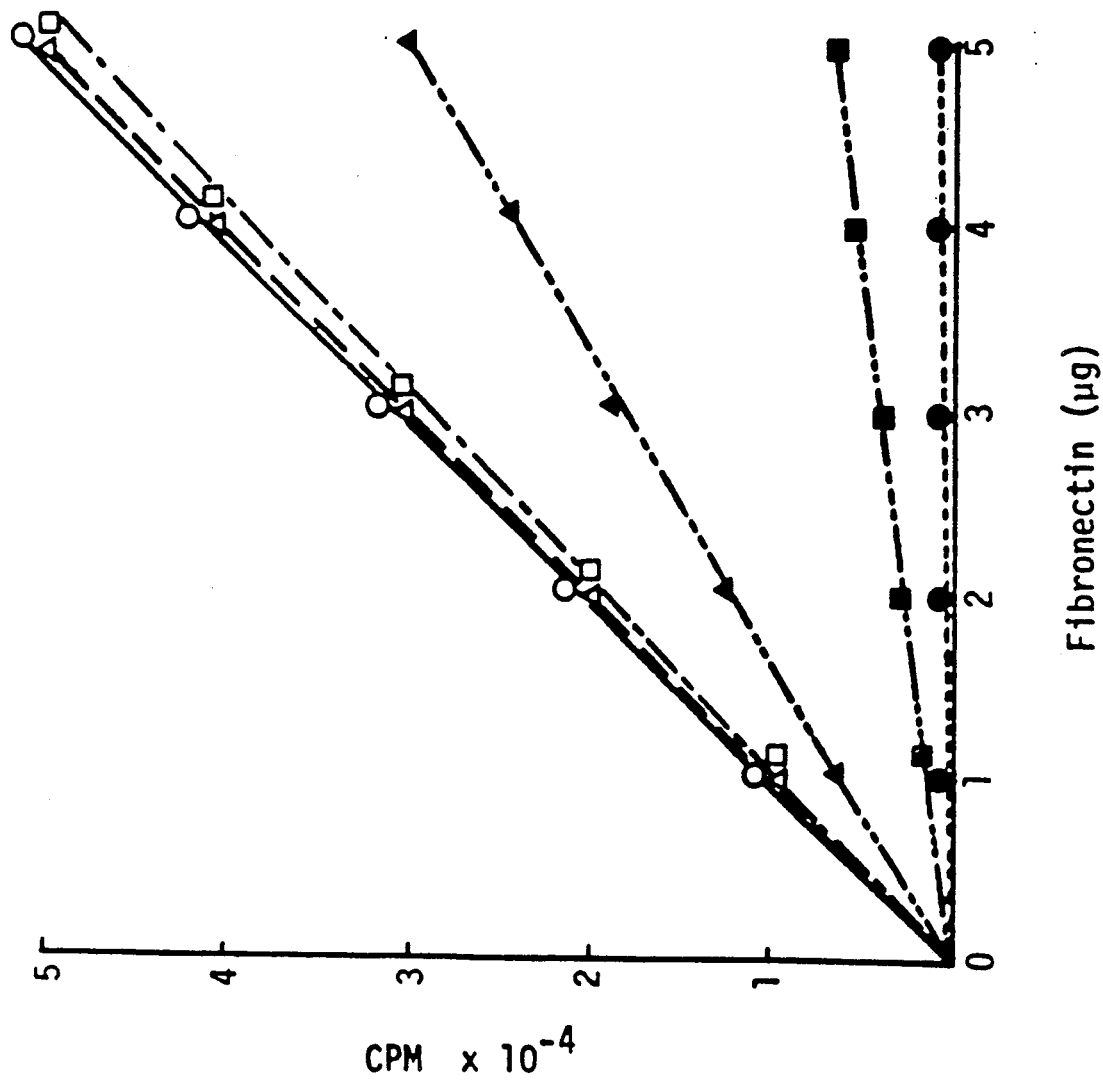

FIG. 13 shows the quantitative reactivity of various fibronectins with monoclonal antibody FDC-6. Fibronectins isolated from culture media of HuH-7, plasma, and various tissue extracts were separated on NaDodSO$_4$/6.5% polyacrylamide gel electrophoresis followed by transfer onto nitrocellulose sheets. Multiple concentrations (1, 2, 3, 4, and 5 $\mu g$) of each purified fibronectin were blotted with the FDZ antibody, and the blotted spots were assayed for radioactivity in gamma counter to determine the activity per $\mu g$. Another panel of multiple immunoblots of fibronectin from each tissue was made with the FDC-6 antibody, and the FDC-6 blotting activity per $\mu g$ of fibronectin was determined. The ordinate indicates the binding activity of each fibronectin with the FDC-6 antibody; the abscissa indicates the quantity of fibronectin per $\mu g$ as determined by binding activity with the FDZ antibody. The various fibronectins are indicated as follows: open circles, HuH; solid circles, plasma; open triangles, placenta; open squares, colon; solid triangles, fetal connective tissue; solid squares, adult connective tissue.

As indicated, fibronectins from colon carcinoma, HuH-7 hepatoma, and placenta showed approximately the same range of binding activity to the FDC-6 antibody per $\mu g$ of fibronectin. The fibronectin from fetal connective tissue showed a lower but obvious activity, whereas fibronectins from adult connective tissue and plasma showed barely detectable binding activity.

EXPERIMENTAL PROCEDURES

Fragmentation of Fibronectins: Thermolysin and trypsin digestion of fibronectins (FNs) was performed as described in Sekiguchi et al., J. Biol. Chem. 258:3967-3973, 1983. Cathepsin D digestion was performed according to Richter et al., Hoppe-Seyler's Z. Physiol. Chem. 362:399-408, 1981. S-Cyanylation was carried out using 2-nitro-5-thiocyanobenzoic acid as described in Sekiguchi et al., Biochemistry 22:1415-1422, 1983. Detailed fragmentation conditions are: FNs (100 μg) were digested with thermolysin (2.5 μg/ml) in 1 ml of 20° mM Tris.Cl (pH 7.8) containing 1.9 mM CAPS, 50 mM NaCl, 0.5 mM EDTA, and 2.5 mM CaCl$_3$ at 22° C. for 0 min, 5 min, 30 min, and 4 h. The enzyme/substrate ratio was 1:40. Digestion was terminated by the additional of EDTA to give a final concentration of 5 mM. FNs (100 μg) were digested with different concentrations of trypsin in 20 mM Tris.Cl (pH 7.8) containing 1.9 mM CAPS, 50 Mm NaCl, and 0.5 mM EDTA at 22° C. for 10 min. Digestion was terminated by the addition of soybean trypsin inhibitor to give a final concentration of 2.5 μg/ml. Trypsin concentrations used were: 0 μg/ml, 1 μg/ml, and 10 μg/ml. FNs (80 μg) were digested with cathepsin D at an enzyme/substrate ratio of 1:250 in 1 ml of 50 mM sodium acetate (pH 3.5) containing 1.8 mM CAPS, 0.5 mM EDTA, and 0.2 mM phenylmethylsulfonyl fluoride at 37° C. for 0 h, 3 h, and 18 h. Digestion was terminated by the addition of 10 times molar excess of pepstatin A and 28 μl of 2.5M Tris.Cl (pH 8.8) to bring the pH to approximately 7.5.

Subfragmentation of the Thermolysin 155K and 145K Fragments: The thermolysin-cleaved 155K/145K fragments were purified by DEAE-cellulose chromatography as described in Sekiguchi et al., J. Biol. Chem. 256:6452-6462, 1981. The purified 155K/145K fragments (3.6 mg) were further digested with thermolysin at an increased protease concentration (15 μg/ml) in 2.7 ml of 25 mM Tris.Cl (pH 7.6) containing 0.5 mM EDTA, 135 mM NaCl, 2.5 mM CaCl$_2$ at 22° C. for 4 h. Digestion was terminated by the addition of EDTA to give a final concentration of 5 mM. The digest was applied to a heparin-Sepharose column (bed volume, 4 ml) equilibrated with 25 mM Tris.Cl (pH 7.6) containing 0.5 mM EDTA and 135 mM NaCl. The bound fragments were eluted with 25 mM Tris buffer containing 1M NaCl. The unbound and bound fragments were separately dialyzed against 10 mM Tris.Cl (pH 7.6) containing 0.5 mM EDTA, lyophilized, and analyzed by SDS-polyacrylamide gel electrophoresis.

While the present invention has been described in conjunction with a preferred embodiment, one of ordinary skill after reading the foregoing specification will be able to effect various changes, substitutions of equivalents, and alterations to the compositions and methods set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. An isolated fragment of oncofetal fibronectin, consisting essentially of the binding region defined by the antibody FDC-6, ATCC No. HB 9018, wherein said binding region is
    (a) located between the thermolysin-defined Hep-2 and Fib-2 domains of oncofetal fibronectin;
    (b) located on the 200,000 dalton trypsin-generated fragment of oncofetal fibronectin; and
    (c) located on the carboxy terminal, disulfide-linked 85,000 and 110,000 dalton cathepsin D generated fragments of oncofetal fibronectin.

* * * * *

UNITED STATES PATENT AND TRADEMARK OFFICE
CERTIFICATE OF CORRECTION

PATENT NO. : 5,243,029
DATED : September 7, 1993
INVENTOR(S) : H. Matsuura et al.

It is certified that error appears in the above-identified patent and that said Letters Patent is hereby corrected as shown below:

| COLUMN | LINE | |
|---|---|---|
| [56] "U.S. Patents" | 2nd Ref. | Please add --4,879,237 5/1985 Rudslahti et al.--. |
| 10 | 25 | "naDodSO$_4$" should read --NaDodSO$_4$-- |

Signed and Sealed this

Fifteenth Day of March, 1994

Attest:

BRUCE LEHMAN

*Attesting Officer*     *Commissioner of Patents and Trademarks*